United States Patent [19]

Shapiro

[11] Patent Number: 5,571,128
[45] Date of Patent: Nov. 5, 1996

[54] SAFETY SURGICAL INSTRUMENT

[76] Inventor: Henry Shapiro, 328 Downham Ct., Walnut Creek, Calif. 94598

[21] Appl. No.: 506,023

[22] Filed: Jul. 24, 1995

[51] Int. Cl.$^6$ ................................................ A61B 17/32
[52] U.S. Cl. ...................... 606/167; 606/170; 606/181; 606/182
[58] Field of Search .................................. 606/167, 170, 606/172, 181, 182; 30/151

[56] References Cited

U.S. PATENT DOCUMENTS

| | | | |
|---|---|---|---|
| 4,499,898 | 2/1985 | Knepshield et al. | 128/305 |
| 4,576,164 | 3/1986 | Richeson | 128/305 |
| 4,674,500 | 6/1987 | DeSainick | 128/305 |
| 5,275,606 | 1/1994 | Abidin et al. | 606/167 |
| 5,309,641 | 5/1994 | Wonderley et al. | 30/339 |
| 5,330,492 | 7/1994 | Haugen | 606/167 |
| 5,330,493 | 7/1994 | Haining | 606/167 |
| 5,391,177 | 2/1995 | Schwartz | 606/167 |

*Primary Examiner*—Michael Powell Buiz
*Assistant Examiner*—Mark S. Leonardo
*Attorney, Agent, or Firm*—George W. Wasson

[57] ABSTRACT

A safety surgical instrument having a sheath, a handle, a surgical element such as a blade or needle, and a manner for moving the surgical element out of and into the sheath by rotary and longitudinal movement of the handle. The control of the movement of the surgical element is accomplished with an insert within the sheath that provides a groove path for cooperation with a part of the handle to move the surgical element in response to rotary and longitudinal movement of the handle. The handle rotary movement is in one direction only to place the surgical element in an unsheathed stop postion and in a sheathed stop position.

19 Claims, 2 Drawing Sheets

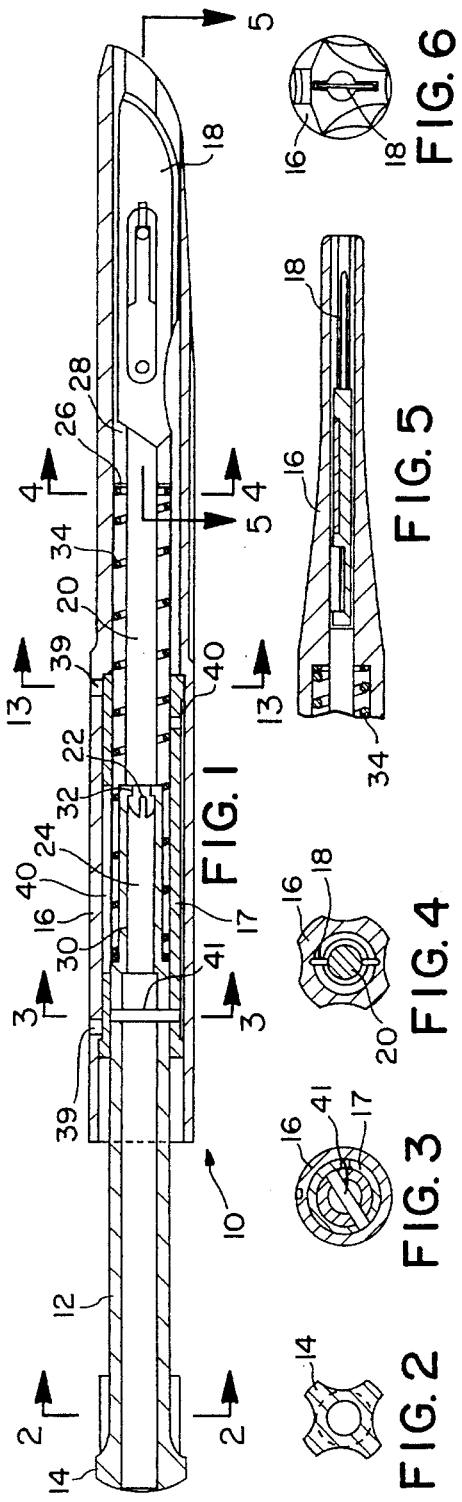
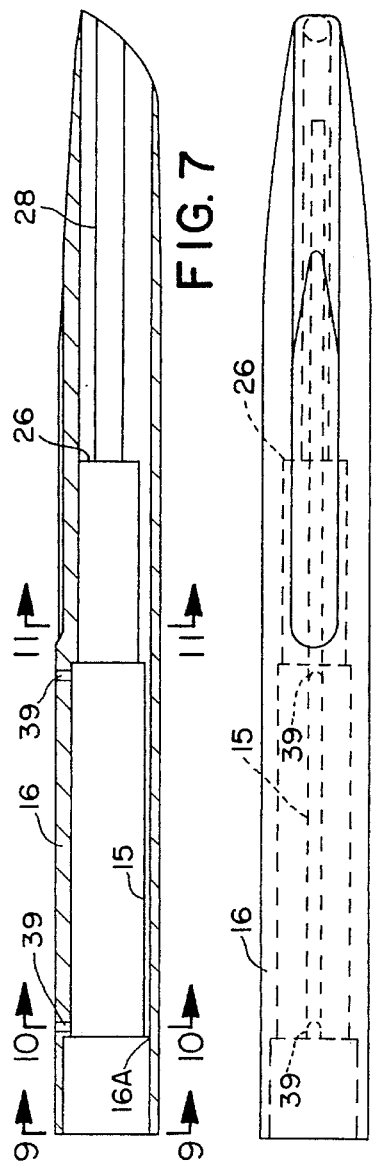
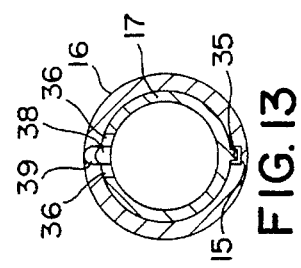
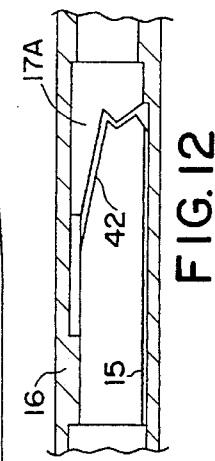
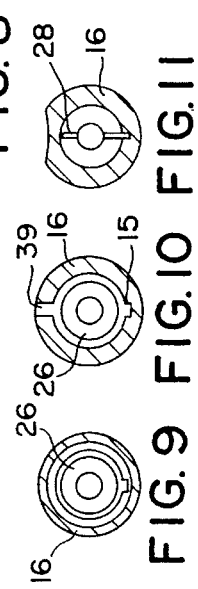

SAFETY SURGICAL INSTRUMENT

FIELD OF THE INVENTION

This invention relates to a surgical instrument and more particularly to a surgical instrument that includes a retractable blade and the means for retaining the retractable blade within a sheath and for moving the retractable blade out of and into the sheath in a safe manner.

BACKGROUND OF THE INVENTION

Scalpels are regularly used by surgeons and other health care professionals for making incissions during an operating procedure. Typically, the operating room assistant passes a scalpel or other surgical instrument to the surgeon's hand in a predetermined orientation, so that the surgeon can grasp the instrument and automatically grip the handle without taking his or her eyes away from the patient or the instrumentation. If the instrument includes a sharp cutting edge or point, it is possible that the surgeon's hand may be cut or nicked in the instrument transfer. Because of such a possibility, sclapels and other surgical instruments have been developed that make the surgical instrument "safe" by keeping the sharp or pointed portion of the instrument enclosed in some form of a sheath during the transfer from the operating room assistant to the surgeon, the surgeon then unsheaths the instrument for use during the operation. The same possible cut or nick can occur during the return of the instrument from the surgeon to the operating room assistant, so it is desireable that the instrument be resheathed for the return transfer.

The concern over possible cuts or nicks has become especially acute since the appearance of the human immune deficiency virus (HIV) as well as other virus such as the Hepatitis B virus (HBV). In some cases, surgeons have stopped performing operations rather than risk the chance of inadvertently being exposed to these viruses.

Several forms of sheathing and sclapel protecting apparatus have been disclosed, some using sliding sheaths and others providing rotatable sheaths to cover the scalpel's cutting surface. One form of such a guard is shown in U.S. Pat. No. 5,330,493, Haining; 5,330,492, Haugen, and 5,275,606, Abidin et al, where a scalpel is enclosed in a guard and a finger operated portion is used to advance and retact the blade form the guard. Each of these patents disclose a advance/retraction mechanism that is reciprocal without rotary movement of a cylindrical instument or sheath. U.S. Pat. Nos. 5,391,177, Schwartz; 5,309,641, Wonderly et al; 4,674,500, DeSatnick; 4,576,164, Richeson; and 4,499,898, Knepshield et al show surgical instruments that include cylindrical sheaths or covers for cutting elements and means for moving the cutting element into and out of the sheath or cover. Of these cylindrical sheath patents, the Richeson, the DeSatnick and the Schwartz disclosures include some form of slot and pin configuration that is reciprocated and rotated to move the functional part of the instrument from the sheathed position to the unsheathed position. In each of the instruments the rotational movement must be reversed to retrieve the instrument to its sheathed position.

The safety surgical instrument of the present invention includes a one-hand operating mechanism that can be used to move a sheathed surgical instrument from its sheathed position to its unsheathed position and the return to the sheathed position by a combination of rotational movement and longitudinal movement with the rotational movement in one direction of rotation only. The instrument includes locking positions in the sheathed position and in the unsheathed position.

SUMMARY OF THE INVENTION

The present invention provides a safety surgical instrument with a mechanism that moves a cutting surface from a sheathed position within the instrument to an unsheathed position through a combination of rotation and longitudinal movement to a first locked position for cutting surface use and then further rotation and longitudinal movement to a locked sheathed position. The instrument includes a hollow sheath, a hollow insert within the sheath and a handle that reciprocates and rotates within the sheath. The insert has a W-shaped groove along its interior or exterior surface and a pin moved with the handle follows the groove to move a blade into or out of the sheath as the handle moves with respect to the sheath. The W-shaped groove is formed to include stop postions for the blade in its unsheathed position and in its sheathed position. The rotation and reciprocal movement of the handle is biased by an internal spring that biases the blade into each of its stop postions and the spring bias forces the blade from its unsheathed position to its sheathed and locked position with only rotary movement of the handle. The instrument is described as a safety surgical instrument because it is easily passed from an operating room assistant to a surgeon in a locked sheathed position and the surgeon may unsheath the cutting blade with one-handed rotary and reciprocal movement to expose the cutting blade and resheath the cutting blade with further rotary movement and release of the handle.

An object of the present invention is the provision of a safety surgical instrument including a means for containing a functional part of the instrument within a sheath and for controllably releasing and returning the functional part to the sheath.

A further object of the present invention in accord with the preceeding object is a means for containing a scalpel or the like within a sheath and a release mechanism that can be operated with one hand of a user.

A further object of the present invention in accord with the preceeding object is a rotary and reciprocal release mechanism that is operated with one direction of rotation of the release mechanism.

A further object of the present invention in accord with the preceeding object is a release mechanism that includes a stop position in the sheathed position and a stop position in the use position.

A further object of the present invention in accord with the preceeding objects is a surgical instrument that is economical to manufacture to the extent that it can be used one time only and discarded after use thus avoiding possibilities of contamination passed from one use to another.

Further objects and features of the present invention will be readily apparent to those skilled in the art from the appended drawings and specification illustrating preferred embodiments wherein:

FIG. 1 is a sectional view through a surgical instrument containing the release mechanism of the present invention.

FIG. 2 is a sectional view taken along the lines 2—2 of FIG. 1.

FIG. 3 is a sectional view taken along the lines 3—3 of FIG. 1.

FIG. 4 is a sectional view taken along the lines 4—4 of FIG. 1.

FIG. 5 is a sectional view taken along the lines 5—5 of FIG. 1.

FIG. 6 is an end view of the forward end of the surgical instrument.

FIG. 7 is a sectional view through the sheath of the surgical instrument.

FIG. 8 is a top plan view of the forward end of the sheath of FIG 7.

FIG. 9 is a sectional view taken along the lines 9—9 of FIG. 7.

FIG. 10 is a sectional view taken along the lines 10—10 of FIG. 7.

FIG. 11 is a sectional view taken along the lines 11—11 of FIG. 7.

FIG. 12 is a sectional view showing an alternative form of construction of a portion of the sheath of the surgical instrument.

FIG. 13 is a sectional view taken along the lines 13—13 of FIG. 1.

DETAILED DESCRIPTION OF THE DRAWINGS

Figure 14:
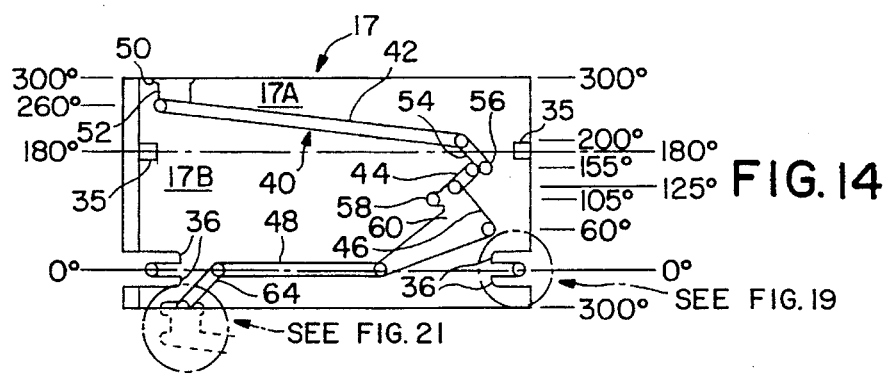
FIG. 14 is a developed view representing the path of the groove of the present invention along an insert as used with the release mechanism.

FIG. 1 illustrates a safety surgical instrument 10 having a forward end at the right side of FIG. 1 and a rear end at the left side of FIG. 1. The instrument includes a handle 12 with a knob 14 at the rear end, a hollow sheath 16, a hollow insert 17, a blade 18 at the forward end, and a blade holder 20 having a connection at 22 to an internal extension 24 of the handle 12. The connection 22 between the extension 24 and the blade holder 20 is adapted to permit the handle to be rotated while the blade holder remains at a fixed radial relationship to the sheath 16. An internal shoulder 26 within the hollow interior of the sheath 16 near the forward end is provided with a radial slot 28 that cooperates with the edges of the flat blade 18 to maintain the blade rotationally fixed with respect to the sheath while permitting the blade to reciprocate into and out of the sheath at the forward end. The handle 12 includes an elongated hollow shaft between the knob 14 and the connection 22 and the shaft has a reduced diameter exterior portion at 30 and a reduced diameter interior opening 32 at the interior end for the connection 22 with the interior end of the blade holder 20. A spring 34 is wrapped around the extension 32 and the blade holder 20 and is held at the rear end against the reduced diameter portion 30 and at the forward end against the shoulder 26. The spring 34 biases the blade holder 20 into the sheath so that the blade 18 is guarded by the sheath at the forward end. The spring 34 also biases the handle 12 out of the sheath so that the relaxed position of the instrument has the handle extended and the blade guarded. The handle is held within the instrument by the engagement of the insert 17 with the sheath 16 as will be described hereinafter.

Within the sheath 16 and between the spring 34 and the interior of the sheath 16 is the hollow tubular insert 17. The insert 17 is fixed to the sheath by suitable means such as registering slots 36 and tabs 37 in the insert 17 that cooperate with complementary fingers 38 and indents 39 or radial holes in the sheath 16, as can be seen in FIGS. 15, 16, 19 and 20 and as will be described hereinafter. Sheath 16 is provided with an axial slot 15 along its inner hollow surface. The insert 17 is provided with a radial registering extension 35. The extension 35 and slot 15 are compementary so that assembly of the insert 17 into the sheath is accomplished by registering the extension 35 of the insert with the slot 15 and sliding the insert axially into the sheath. When the insert 17 reaches its forward position, the complementary fingers 38 of the sheath are aligned with the registering slot 36 and the tabs 37 on the insert are aligned with indents 39 in the inner surface of the sheath 16.

The insert 17 has a patterned groove 40 formed in its surface, either interior or exterior as will be described hereinafter, to provide a guide path for reciprocal and possible rotary movement of the handle 12 with respect to the insert 17. In the form of apparatus shown in FIG. 1, a pin 41 is contained in the handle 12 and aligned with the groove 40 in the insert 17. Axial movement of the handle 12 causes the pin 41 to be moved along the groove 40 and to move the blade holder 20 out of the sheath 16 against the bias of spring 34 to place the blade 18 in a use position. Release of the handle 12, except as will be described later, causes the bias of spring 34 to force the blade 18 back into the sheath 16.

As shown in developed view FIG. 14, the groove 40 in the insert 17 is formed in a W-shaped pattern having a first outer leg 42 at the upper end of the FIG. 14, a first inner leg 44 joined to leg 42, a second inner leg 46 joined to leg 44, and a second outer leg 48 joined to leg 46. It should be understood that the developed view of FIG. 14 is as though the hollow cylindrical insert were laid out flat whereas, in reality, the insert is as is shown in FIGS. 17 and 18 where FIG. 17 illustrates one side of the cylindrical insert and FIG. 18 illustrates the other side of the insert and as though FIG. 17 was rotated 180°.

Figure 15:
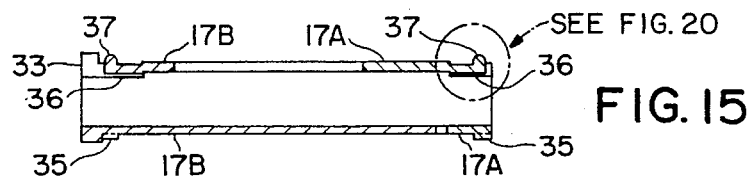
FIG. 15 is a sectional view of an insert formed of two complementary parts.
Figure 16:
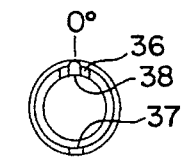
FIG. 16 is an end view of the inserts of FIG. 15.
Figure 17:
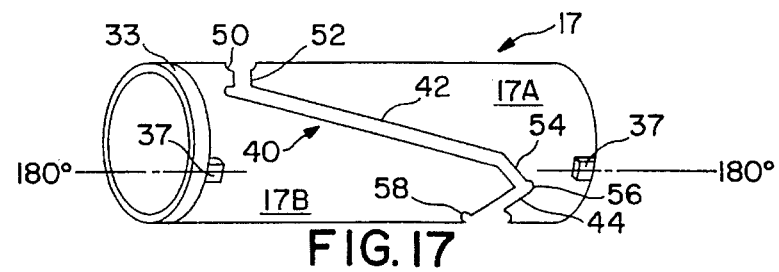
FIG. 17 is a perspective view illustrating one half of the groove along the surface of the insert of the present invention.
Figure 19:
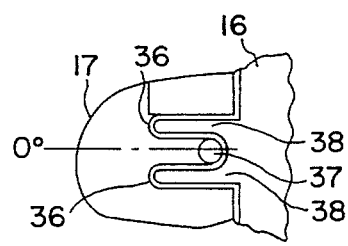
FIG. 19 is an enlarged view showing the registering means for each end of the insert of FIG. 14.
Figure 18:
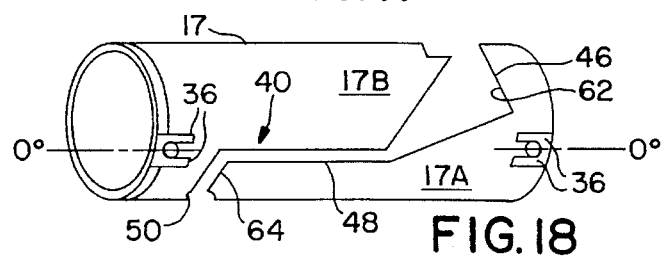
FIG. 18 is a perspective view illustrating the other half, as compared to FIG. 17, of the groove along the surface of the insert of the present invention.
Figure 20:
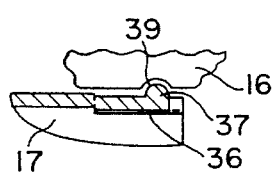
FIG. 20 is an enlarged view showing a section through the registering means for each end of the insert of FIG. 14.

At the rear end of the insert, at the upper left of FIG. 15 and FIG. 17 the first outer leg 42 is formed with a rear end stop 50 connected by a horizontal groove 52 to the top of the outer leg 42. The forward end of the first outer leg 42 is formed with an inclined portion 54 and an axial groove 56 leading to the first inner leg 44. The junction of the first inner leg 44 and the second inner leg 46 is formed with a widened axial groove 58 that functions as a forward end stop position, as will be described hereinafter. The second inner leg 46 is a widened portion of the groove at 60 to form a stop release portion of the groove and a connection to the axial portion of the second outer leg 48 at an inclined portion 62. The rear end of the second outer leg 48 is formed with an inclined portion 64 leading to the rear end stop 50. The return to the rear end stop 50 brings the W-shaped groove back to its beginning as though the two outer legs 42 and 48 were joined.

With pin 41 aligned and cooperating with the groove 40 at the rear end stop 50 and with rotation of the handle 12, the pin 41 is passed from the stop postion 50 to the horizontal groove 52 to the start of the first outer leg 42. Axial movement of the handle 12 will then cause the handle to rotate as it follows the leg 42 to the axial groove 56 where release of the handle will force the handle to the rear under the bias of spring 34 to place pin 41 in the forward end stop position at 58; in that position the blade 18 is exposed from the sheath 16.

When the blade is to be retracted, the handle 12 is moved axially toward the forward end forcing the pin 41 out of the stop position 58 and into engagement with the inclined portion 62; that engagement causes the handle 12 to be rotated to align the pin 41 with the second outer leg 48. Release of the handle 12 then causes the pin 41 to be moved along the leg 48 under the bias of the spring 34 until the pin engages the inclined portion 64 moving the pin 41 to the rear end stop postion 50 where it began. The blade 18 is now retracted into the sheath 16 in a safe position for handling.

The movement of the pin within the groove by the rotation, axial movement and release of the handle 12 can be done by the user with one hand holding the sheath 16 between the palm of the hand and some fingers while the handle 12 is rotated and axially moved with the thumb and first finger.

While the insert 17 has been described as a hollow cylindrical element, it should be understood that the insert can be formed with two separate portions 17A and 17B positioned within the sheath and secured by separate complementary registering extensions 35 and slots 36 in the insert pieces cooperating with complemetary fingers 38 in the sheath. The separate pieces of the insert are locked in place by alignment of extensions 35 with the groove 15 in the sheath 16 and axially placing the insert into position with tabs 37 in the inserts engaged with indents 39 in the inner surface of the sheath. The rear end of the insert 17B includes a radial collar 33 that registers with the reduced diameter shoulder 16A of sheath 16. When the collar 33 engages the shoulder 16A, the tab 37 is in position to be registered with the indent 39 in the sheath 16. When positioned and fixed in place the two piece insert provides the equivalent of the continuous cylindrical insert. It should be evident that the manufacture of a cylinder with the continuous groove 40 either in the exterior or interior of a cylinder can be difficult. Stamping or cutting the groove pattern in a flat sheet and then rolling the pieces into portions of a cylinder is not difficult and the positioning of the two parts within a sheath with extensions cooperating with a stop and alignment slots, fingers, tabs and indents can produce the desired continuous groove 40 from two separate parts.

Another alternative form for developing the groove 40 is shown in FIG. 12 where an insert is partially formed with the sheath, the forward portion of the insert is formed into the interior hollow surface of the sheath. Formation of the sheath 16 with a molding apparatus can produce the desired contour for one part of the groove 42 with the portion 17A of the sheath forming the forward end of the groove. The other part of the groove 40 can be formed with a one piece insert 17B in the form of that shown at the left of FIGS. 14, 15, 17 and 18. The single piece insert 17B will than be placed into the interior of the sheath 16 and locked in place with the described slots, fingers, tabs and detents.

Figure 21:
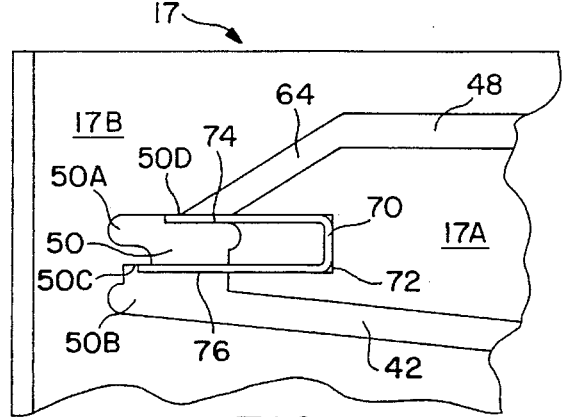
FIG. 21 is an enlarged view showing the one-way barrier in the insert of the present invention.

FIG. 21 is an enlarged portion of FIG. 14 representing the junction of legs 64 and 42 to form rear end stip 50. FIG. 12 illustrates a one-way resilient barrier 70 inserted axially along the insert 17 so as to fit into the portion 17A in a complementary slot 72 with resilient legs 74 and 76. Leg 74 extends into the groove 40 at the exit from leg 64 into the stop position 50 with the end of that leg engaging the shoulder between the leg 64 and portion 50A of the rear end stop position 50. Leg 76 extends into the groove 40 before the beginning of leg 42 with the end of that leg engaging a shoulder 50C between the portion 50A and portion 50B of the rear end stop position 50. When the pin 41 is travelling along leg 48 and into inclined portion 64 under the bias of spring 34, it engages leg 74 of barrier 70 and bends that leg to enter into portion 50A of the rear end stop position. The pin cannot reenter leg 64 because the leg 74 of the barrier is in contact with shoulder 50D and the barrier blocks the entry into that portion of the groove 40. When it is desired to rotate and press the handle 12 to move the blade from the sheath, the pin 41 is rotated from portion 50A into portion 50B moving leg 76 of the barrier 70. The pin can then enter portion 50B and be passed along leg 42 to the forward stop position. The pin 41 cannot reenter portion 50A because leg 76 of the barrier engages shoulder 50C to prevent that entry.

While the safety surgical instrument has been described as useful in sheathing and exposing a blade in the form of a scalpel, it should be understood that many different forms of surgical instruments with sharp or pointed ends can be moved into and out of a sheath with the embodiment described. Such instruments can include an MVR cutting blade, a needle, a probe, and other instruments that are used in opthalmic, arthroscopic and other surgical proceedures. The instrument as described can be inexpensively manufactured and assembled and can be treated as a single use instrument that will be discarded after use. Even if discarded, the instrument will be sheathed in the transfer to the surgeon and in return to the assistant to protect against accidental cutting, puncture or nicking.

If the surgical portion of the instrument does not need to be oriented as a scalpel would be oriented, there will not be a need for a rotary connection between the handle extension 24 and the blade holder 20. It is also possible to form the groove 40 in the exterior or interior of the cylindrical surface of the insert 17 and the groove can be followed by a pin in the handle as described or in the interior of the sheath 16. In that form the insert would move with respect to the pin and carry the blade out of and into the sheath. Another alternative is to form the slot 40 along the interior of the sheath 16 and to provide a pin 41 in the handle extension. The handle pin 41 would follow the groove 40 as described in the case of the grooved insert.

While certain preferred embodiments of the invention have been specifically disclosed, it should be understood that the invention is not limited thereto as many variations will be readily apparent to those skilled in the art and the invention is to be given the broadest possible interpertation within the terms of the following claims.

I claim:

1. A safety surgical instrument comprising:

a) a hollow sheath having a forward end and a rear end and a longitudinal axis, b) a hollow insert having a forward end and a rear end and a longitudinal axis, said insert being fixed within said seath with said insert longitudinal axis aligned with said sheath longitudinal axis, c) a handle, said handle being axially aligned with said sheath and adapted to be longitudinally and rotatably movable within said insert, d) a blade, said blade being longitudinally movable with said handle with respect to said sheath, e) a W-shaped cutout axially along said insert, said cutout being radially from said insert longitudinal axis, f) a pin extending radially from said handle, said pin being aligned with and cooperating with said cutout along said insert, g) a spring, said spring being positioned between said handle and said sheath and biasing said handle and said blade within said sheath from said forward end toward said rear end, h) said W-shaped cutout in said insert defining a continuous cutout groove within said insert and 360° around said insert, the ends of the outer legs of said W-shaped cutout connecting with each other and forming a rear end stop position within said cutout, the junction of the inner legs of said W-shape being at about 180° around said insert and forming a forward end stop position within said cutout, i) whereby initial rotation and depression of said handle causes said pin to pass along an outer leg of said W-shaped cutout from said rear end stop position to said forward end stop position against the bias of said spring to move said blade from said sheath, and a second depression of said handle causes said pin to pass along said inner leg of said W-shape to rotate said handle and move said pin to said rear end stop postion under the bias of said spring and to move said blade into said sheath.

2. The surgical instrument of claim 1 wherein the rear end of a first of said outer legs of said W-shaped cutout includes a lock position, an inclined portion and an axial groove to a first of said inner legs, a widened groove along said first of said inner legs to said forward end stop position, an inclined portion along the second of said inner legs to a front end stop release position at a connection of said second of said inner legs with the second of said outer legs, and an inclined portion of said second of said outer legs to said rear end stop position.

3. The surgical instrument of claim 1 wherein said insert is a two part element secured within said sheath, each part of said two part insert being formed with said cutout contour and the spacing of said two parts of said insert within said sheath forming said groove within said insert.

4. The surgical instrument of claim 1 wherein said insert is a one part element cooperating with a formed portion of the inner surface of said hollow sheath, said insert and formed portion of said sheath being contoured to produce said W-shaped contour and being aligned and spaced so as to form said groove for cooperation with said pin in said handle.

5. The surgical instrument of claim 1 wherein said insert is formed with said cutout on the inner surface of said insert and said pin is in said handle and cooperating with said cutout along said inner surface.

6. The surgical instrument of claim 1 wherein said insert is formed with said cutout along the outer surface of said insert and said pin is in said sheath, said handle moving said insert to cause said blade to move from said sheath and to return said blade into said sheath.

7. The surgical instrument of claim 1 wherein said sheath is formed with said groove and said pin is in said handle in cooperation alignment with said groove.

8. The surgical instrument of claim 1 wherein said handle and said blade include a rotatable connection whereby said handle may rotate as said handle enters said insert and said blade reciprocates into and out of said sheath as said handle moves within said sheath.

9. The surgical instrument of claim 1 wherein said handle and said blade are connected to extend said blade from said sheath and retract said blade into said sheath with movement of said handle.

10. The surgical instrument of claim 1 wherein said blade is a scalpel.

11. The surgical instrument of claim 1 wherein said blade is a MVR knife.

12. The surgical instrument of claim 1 wherein said blade is a needle shaped element.

13. The surgical instrument of claim 1 wherein said insert is formed as a flat element with said cutout groove along a flat surface, said flat element is then rolled into a cylindrical form for insertion into said sheath.

14. The surgical instrument of claim 1 wherein said insert is formed with alignment elements along its forward and rear end surfaces, and said sheath is formed with alignment elements along its forward and end inner surfaces, said alignment elements of said insert and said sheath being complementary so as to align said insert within said sheath when said surgical instrument is assembled.

15. The surgical instrument of claim 1 wherein:

a) said insert has a radial extension and said sheath has a longitudinal slot, said extension in said insert being aligned with said slot in said sheath for registering said insert within said sheath, b) said insert has axial slots and said sheath has axial fingers, said insert slots and said sheath fingers being complementary and adapted to align said insert within said sheath, c) outwardly extending tabs on said insert and indents along said hollow interior of said sheath, said tabs cooperating with said indents to retain said insert within said sheath.

16. The surgical instrument of claim 1 wherein said junction of said outer legs of said W-shaped cutout includes a one-way resilient barrier within said groove, said one-way resilient barrier permitting said pin to enter said junction of said outer legs when returning from said junction of said inner legs and to enter said outer leg of said W-shaped cutout from said rear end stop position to said forward end stop position, said one-way resilient barrier prohibiting movement of said pin in a reverse direction from said junction of said outer legs.

17. The surgical instrument of claim 4 wherein said sheath is an injection molded element formed with said contoured surface along its inner forward end, said contoured surface being complementary with said contoured insert to form said W-shaped groove.

18. The surgical instrument of claim 1 wherein said W-shaped groove formed by said insert includes a first outer leg having a sloping axial path to said forward end stop position, and a second outer leg having an axial path to a rear end sloping path to said junction with said first outer leg, said movement along said first outer leg sloping axial path being against said bias of said spring and said movement along said second outer leg being forced by said bias of said spring.

19. The surgical instrument of claim 1 wherein said forward end stop postion at said junction of said inner legs of said W-shape is entered and retained under said bias of said spring, and the exit from said forward end stop position is against said bias of said spring to a surface within said second inner leg to a position for entry into said second outer leg under said bias of said spring and return to said rear end stop position.

* * * * *